United States Patent
Giles

(10) Patent No.: US 10,607,828 B2
(45) Date of Patent: Mar. 31, 2020

(54) COUPLING INTERMEDIATE PRESSURE REGIONS

(71) Applicant: Micromass UK Limited, Wilmslow (GB)

(72) Inventor: Kevin Giles, Stockport (GB)

(73) Assignee: MICROMASS UK LIMITED, Wilmslow (GB)

( * ) Notice: Subject to any disclaimer, the term of this patent is extended or adjusted under 35 U.S.C. 154(b) by 50 days.

(21) Appl. No.: 15/170,133

(22) Filed: Jun. 1, 2016

(65) Prior Publication Data

US 2016/0351382 A1 Dec. 1, 2016

(30) Foreign Application Priority Data

Jun. 1, 2015 (GB) .................................. 1509412.1

(51) Int. Cl.
| | |
|---|---|
| *H01J 49/24* | (2006.01) |
| *G01N 27/62* | (2006.01) |
| *H01J 49/00* | (2006.01) |
| *H01J 49/04* | (2006.01) |

(52) U.S. Cl.
CPC ............ *H01J 49/24* (2013.01); *G01N 27/622* (2013.01); *H01J 49/005* (2013.01); *H01J 49/0495* (2013.01)

(58) Field of Classification Search
CPC ...... H01J 49/24; H01J 49/005; H01J 49/0495; G01N 37/622
See application file for complete search history.

(56) References Cited

U.S. PATENT DOCUMENTS

| | | | | |
|---|---|---|---|---|
| 5,596,193 | A * | 1/1997 | Chutjian | H01J 49/0013 250/281 |
| 5,719,393 | A * | 2/1998 | Chutjian | H01J 49/0013 250/281 |
| 7,339,163 | B2 * | 3/2008 | Marriott | H01J 49/0045 250/281 |
| 8,604,419 | B2 * | 12/2013 | Nolting | H01J 49/0072 250/282 |
| 8,610,053 | B2 * | 12/2013 | Yamada | H01J 49/0495 250/281 |
| 9,123,523 | B2 * | 9/2015 | Green | H01J 49/0059 |
| 9,269,551 | B2 | 2/2016 | Ueda | |

(Continued)

FOREIGN PATENT DOCUMENTS

| | | | |
|---|---|---|---|
| GB | 2506466 | A * | 4/2014 |
| JP | 2012043672 | | 3/2012 |

OTHER PUBLICATIONS

"Chamber." Merriam-Webster.com. Merriam-Webster, n.d. Web. Aug. 24, 2018.*

(Continued)

*Primary Examiner* — Wyatt A Stoffa
(74) *Attorney, Agent, or Firm* — Womble Bond Dickinson (US) LLP; Deborah M. Vernon; Heath T. Misley

(57) ABSTRACT

A method is disclosed for coupling a first chamber of a mass spectrometer or ion mobility spectrometer containing a first gas and a second chamber containing a second gas. The method comprises providing an intermediate region between the first and second chambers that is operated at a lower pressure to substantially prevent or reduce ingress of the first gas into the second chamber and/or of the second gas into the first chamber.

10 Claims, 4 Drawing Sheets

(56) References Cited

U.S. PATENT DOCUMENTS

| | | | | |
|---|---|---|---|---|
| 9,842,730 B2* | 12/2017 | Schoen | | H01J 49/005 |
| 2004/0031917 A1* | 2/2004 | Hager | | H01J 49/0031 |
| | | | | 250/282 |
| 2004/0069943 A1* | 4/2004 | Kato | | H01J 49/0095 |
| | | | | 250/281 |
| 2004/0245452 A1* | 12/2004 | Bateman | | G01N 27/622 |
| | | | | 250/287 |
| 2007/0138383 A1* | 6/2007 | Dowell | | H01J 49/0072 |
| | | | | 250/281 |
| 2010/0032561 A1* | 2/2010 | Giles | | H01J 49/4235 |
| | | | | 250/283 |
| 2011/0210243 A1* | 9/2011 | Colby | | H01J 49/005 |
| | | | | 250/282 |
| 2012/0138790 A1* | 6/2012 | Wright | | H01J 49/0013 |
| | | | | 250/288 |
| 2012/0193526 A1* | 8/2012 | Kovtoun | | H01J 49/005 |
| | | | | 250/282 |
| 2013/0053542 A1* | 2/2013 | Attygalle | | H01J 49/0459 |
| | | | | 530/300 |
| 2014/0145074 A1* | 5/2014 | Giles | | H01J 49/4235 |
| | | | | 250/282 |
| 2014/0217280 A1* | 8/2014 | Sugawara | | H01J 49/005 |
| | | | | 250/288 |
| 2015/0097114 A1* | 4/2015 | Green | | H01J 49/0059 |
| | | | | 250/282 |
| 2015/0136966 A1* | 5/2015 | Badiei | | H01J 49/005 |
| | | | | 250/281 |
| 2015/0136973 A1* | 5/2015 | Lin | | H01J 49/0495 |
| | | | | 250/282 |
| 2016/0320294 A1* | 11/2016 | Schlueter | | G01N 21/3504 |
| 2017/0200594 A1* | 7/2017 | Giles | | H01J 49/0009 |
| 2017/0301528 A1* | 10/2017 | Badiei | | H01J 49/005 |

OTHER PUBLICATIONS https://web.archive.org/web/20141229070014/https://en.wikipedia.org/wiki/Pressure_gradient (Year: 2014).* https://web.archive.org/web/20141226175721/https://en.wikipedia.org/wiki/diffusion (Year: 2014).*

* cited by examiner

COUPLING INTERMEDIATE PRESSURE REGIONS

CROSS-REFERENCE TO RELATED APPLICATION

This application claims priority from and the benefit of United Kingdom Patent Application No. 1509412.1 filed on 1 Jun. 2015. The entire contents of this application are incorporated herein by reference.

FIELD OF THE INVENTION

The present invention relates generally to mass or ion mobility spectrometers and in particular to methods and apparatus for coupling gas-filled regions within mass or ion mobility spectrometers.

BACKGROUND

It is common for mass spectrometry instruments to have various regions operating at different pressures along the length of the instrument. For instance, the source region may be operated at relatively high or atmospheric pressure, whereas the analyser region may be operated under high vacuum conditions (i.e. very low pressures). Various regions, for instance regions used for transportation and/or manipulation of ions, may be provided between the source and analyser regions that are operated at intermediate pressures.

For example, WO 2013/171495 (MICROMASS) discloses a mass spectrometer in which ions generated at an ion source are passed in sequence through a first vacuum chamber via an ion transfer ion guide, into a second vacuum chamber containing a quadrupole mass filter, into a gas collision cell, into an ion mobility separation device and a second gas collision cell before finally arriving at the mass analyser, with each of these devices/regions being operated at various pressures. The operating pressure in each region is selected according to the purpose of that region.

Other instruments having multiple pressures along the length of the instrument are disclosed e.g. in US 2013/0175442 (AGILENT), WO 00/16375 (VG ELEMENTAL), JP 2012-043672 (SHIMADZU) and WO 2014/080493 (SHIMADZU).

In some cases background gas may be allowed to flow freely between the different pressure regions. This gas may be used to carry ions in the direction of gas flow. For example, this may be exploited in the first vacuum stages of a mass spectrometer. In these instances the gas composition in sequential regions may be very similar.

In other cases, gases may be controlled such that they are prevented from entering another region by an outflow of gas from that region. For example, where ion mobility separation ("IMS") devices are operated in the first vacuum stages of a mass spectrometer, ingress of source gas into the ion mobility separation device is prevented by excess pressure/flow of the ion mobility separation buffer gas. In this case, the ion mobility separation gas enters the previous or upstream region. This may also be the case where a high pressure ion mobility separation device is situated downstream of a low pressure quadrupole region.

It will be appreciated that in each of these cases there is an intermixing of gases between adjacent regions.

It is desired to provide improved methods of coupling gas-filled regions.

SUMMARY

According to an aspect there is provided a method for coupling gas-filled regions within a mass spectrometer or an ion mobility spectrometer comprising:

providing an intermediate region disposed between a first chamber containing a first gas and a second chamber containing a second gas; and operating the intermediate region at a pressure below that of the first and second chambers so as to substantially prevent or reduce ingress of the first gas into the second chamber and/or of the second gas into the first chamber.

The techniques and devices described herein allow first and second chambers filled respectively with first and second gases to be connected in such a way that ions can be readily and efficiently transferred from one chamber to the other whilst preventing intermixing of the first and second gases in the first and/or second chambers. This is achieved by providing a lower pressure intermediate region between the first and second chambers that serves as a "gas bridge". Preventing transfer of either gas into the other chamber can, for example, allow the purity of the gas in both chambers to be maintained. Maintaining gas purity can, for example, allow better control over the analyte ions within the first and/or second chambers.

In known instruments, such as that described in WO 2013/171495 (MICROMASS), for example, the pressures in the different regions are simply chosen depending on the purpose of that region. For instance, in WO 2013/171495 (MICROMASS) the ion mobility drift cell, where ions are arranged to interact with the buffer gas molecules is operated at a relatively high pressure of around 2 mbar. However, the filtering and analysis regions, where interactions with background gas are to be avoided, are operated at much lower pressures, e.g. less than $10^{-4}$ mbar in the first mass filter and less than $10^{-6}$ mbar in the Time of Flight mass analyser.

By contrast therefore, the pressures and pressure differences in WO 2013/171495 (MICROMASS) are not selected or controlled so as to substantially prevent or reduce ingress of first gas from a first chamber into a second chamber and/or of second gas from a second chamber into a first chamber, and there are no intermediate regions provided between first and second chambers that are configured to operate in this manner.

The techniques described herein are also, in embodiments, particularly concerned with coupling adjacent regions of relatively high pressures, e.g. within the range of about $10^{-2}$ to $10^3$ mbar. For instance, such pressures may be used in regions where it is desired to cause analyte ions to interact with the gas molecules—e.g. an ion mobility separation, ion cooling, or ion activation region. At these pressures, and especially towards the higher sub-ranges, of e.g. 0.5 mbar upwards, it has been recognised that the gas outflow from the chambers may be viscous or laminar, which may make it difficult to transport ions between the chambers (i.e. against the gas outflow). Attempting to increase the driving force may result in unwanted activation of the ions, again, in part due to the relatively high pressures involved.

Thus, in embodiments, an intermediate pressure region also operating at a similarly, relatively high pressure (but still lower than that of the first and second chambers) is provided, such that the gas flow can be set up to prevent intermixing of gases between the first and second chambers whilst retaining the ability to transport ions without unwanted loss or activation.

Accordingly, the method may comprise: operating the first chamber at a pressure within the range of about $10^{-2}$ to $10^3$ mbar; and/or operating the second chamber at a pressure within the range of about $10^{-2}$ to $10^3$ mbar; and/or operating the intermediate region at a pressure within the range of about $10^{-3}$ to $10^3$ mbar and below the pressures at which each of the first and second chambers are operated.

In embodiments, the first and second chambers are both operated at a pressure within the range of about $10^{-2}$ to $10^3$ mbar, and the intermediate region is optionally also operated at a pressure within the range of about $10^{-2}$ to $10^3$ mbar (but below the pressures at which each of the first and second chambers are operated).

WO 2013/171495 (MICROMASS) is not concerned with coupling two relatively high pressure chambers operating in the range of about $10^{-2}$ to $10^3$ mbar. It will be appreciated that most of the regions described in WO 2013/171495 (MICROMASS) are operated at relatively low pressures, where there would be relatively low gas outflow, typically under molecular flow conditions. This is a different pressure regime, where different considerations apply. This applies similarly to the other documents discussed in the Background section above.

It will be appreciated that the techniques and devices described herein may be used for coupling a number of high pressure regions that are located downstream of the ion source and/or of one or more relatively low pressure regions. Transporting ions into the downstream high pressure regions, against the pressure gradient, may be relatively inefficient in itself, but then repeatedly transporting ions from low pressure to high pressure regions multiple times may compound this problem. By having multiple high pressure regions coupled to each other using the techniques described herein, the pressure gradients between the high pressure regions can be reduced to facilitate the transportation of ions between the high pressure regions.

The intermediate region may be operated at a pressure low enough such that there is only gas outflow from the first and second chambers, but not so low that transport of ions is hindered. The method may comprise operating the intermediate region at a pressure such that ions can be efficiently transported between the first and second chambers without causing undesired ion loss or activation.

Accordingly, the first chamber, second chamber and intermediate region may be configured such that ions can be transferred between the first chamber and/or the second chamber and the intermediate region without causing unwanted activation or loss of ions. That is, the pressures and/or any driving forces or fields may be chosen to facilitate ion transport between the first and/or second chamber and the intermediate region.

Operating the intermediate region at a lower pressure may comprise maintaining a certain minimum and/or maximum pressure difference between the intermediate region and the first and second chambers, or maintaining the intermediate region within a certain pressure difference range relative to the first and/or second chamber. The pressure difference may be selected to ensure that ions can be transported from the intermediate region to the first and/or second chamber efficiently and/or using relatively low electric fields so as to prevent unwanted ion activation.

The minimum and/or maximum pressure difference may be selected such that the gas flow from the first and/or second chambers to the intermediate region occurs under transitional or viscous gas flow conditions. For instance, the Knudsen number of the gas flow from the first and/or second chamber to the intermediate region may be less than about 5, less than about 2.5, less than about 1, less than about 0.5, or less than about 0.1. The Knudsen number is defined as the ratio of the mean free path of the gas molecules and the diameter of the aperture through which the gas molecules flow.

It will be appreciated that transitional or viscous gas flow conditions typically occur at relatively high pressures, and where there are relatively low pressure differences between adjacent regions. At lower pressures, the gas flow may typically occur under molecular flow conditions. Where there are large pressure differences, between different pressure regimes, e.g. when providing a high or intermediate pressure ($10^{-2}$ to $10^3$ mbar) region adjacent to a low vacuum pressure region (e.g. less than $10^{-3}$ mbar), as may be the case in conventional instrument geometries, including e.g. many of those discussed in the Background section above, the flow may also become more turbulent. The techniques described herein may prevent or reduce turbulent flow of the first and/or second gases between the first and second chambers or into the intermediate region.

It will be understood that a chamber is generally an enclosed space into which gas may be provided. The first and second chambers may generally comprise entrance and exit apertures through which ions pass into/out of the chamber. The first and second gases can also pass through these apertures, and in various embodiments the first and second gases may only exit the first and second chambers via these apertures. However, the first and second chambers may also be pumped, e.g. using a pump. The first and second chambers are thus in fluid communication with the intermediate region. However, the first and second chambers may otherwise be substantially gas tight. By providing an intermediate region between the first and second chambers it will thus be understood that the intermediate region may be generally disposed between facing apertures of the first and second chambers.

The first chamber may have a dedicated gas supply for supplying the first gas.

The second chamber may have a dedicated gas supply for supplying the second gas.

That is, the first and second gases may each be supplied directly (and independently) to the first and second chambers by a respective gas supply, e.g. rather than being provided via an adjacent or further chamber. In this way, the gas composition and/or pressure within the chamber may be more accurately controlled, which again may help to maintain gas purity.

The first and second chambers may be respectively operated at first and second pressures. The first and/or second pressure may be regulated by pumping the first and/or second chamber, or by pumping the intermediate region. The first and/or second pressures may additionally or alternatively be controlled via the first and/or second gas supply.

The first and/or second chambers may generally comprise a plurality of electrodes for confining, manipulating and/or transporting ions.

The second chamber may be disposed downstream of the first chamber, e.g. so that, in use, ions pass from the first chamber to the second chamber. However, various other instrument geometries are also contemplated. For instance, the second chamber may be arranged so that in a first mode of operation ions pass to the second chamber and in a second mode of operation ions are arranged to bypass the second chamber. The first and second chambers may also be provided as part of a cyclic or multi-pass instrument geometry. It will be appreciated that multiple regions or chambers may be coupled using a single intermediate region. For instance, the method may comprise providing another chamber containing a further gas, in fluid communication with the intermediate region and operating at a pressure such that ingress of the first and/or second gas into said another chamber is substantially prevented or reduced, and/or such that ingress of the further gas into the first and/or second chamber is substantially prevented or reduced.

The first gas may be different to the second gas. For example, one gas may comprise or essentially consist of nitrogen and the other gas may comprise or essentially consist of helium. In this case, it may be important to prevent intermixing of the gases to keep the gas composition pure, e.g. where the gas is used as an ion mobility buffer gas. It is also contemplated, however, that the first gas may be the same as the second gas. In this case it may be desired to prevent mixing of the gases e.g. to avoid pressure fluctuations or within an ion activation region.

Operating the intermediate region at a pressure below that of the first and second chambers may comprise pumping the intermediate region.

The intermediate region may be connected to or in communication with a vacuum pump and the method may comprise pumping the intermediate region using the vacuum pump. The vacuum pump may have a variable pumping speed. The method may comprise adjusting the pumping speed to control the pressure within the intermediate region. One or more pressure/flow sensors and/or a feedback loop may be provided for controlling the pumping of the intermediate region to keep the pressure (difference) within a desired range.

The first and second chambers may be enclosed within a further chamber containing the intermediate region. In this case the intermediate region may thus be defined by the portion of the further chamber situated between the first and second chambers i.e. between facing apertures thereof. Pumping the chamber containing the first and second chambers and the intermediate region will thus reduce the pressure in the intermediate region. It will be appreciated that the pressure in the intermediate region may generally be locally higher than that elsewhere within the chamber due to the gas flow from the first and second chambers.

The intermediate region may comprise a third chamber. The third chamber may be in fluid communication with the first and second chambers via respective apertures in the first, second and third chambers. Where the intermediate region comprises a third chamber, the third chamber may not have a dedicated gas supply, but may simply receive gas from the first and second chambers. However, the third chamber may be provided with a dedicated gas supply, e.g. to help maintain the pressure in the third chamber. The chambers may be of substantially equal (radial) dimensions and arranged in-line. However, various other suitable arrangements are also contemplated.

The method may comprise: (i) passing ions from the first chamber to the second chamber via the intermediate region; (ii) passing ions from the second chamber to the first chamber via the intermediate region; or (iii) passing ions from the first and/or second chamber to another region via the intermediate region.

The method may comprise applying an electric field to the intermediate region and/or between the first and second chambers in order to pass ions between the first chamber and the second chamber via the intermediate region.

The ions may be driven through or out of the intermediate region by one or more electric fields or potentials applied to electrodes of the intermediate region. For instance, the ions may be driven using one or more linear DC gradients, one or more transient DC potentials ("travelling waves") and/or one or more AC or RF potentials.

The ions may additionally/alternatively be driven from the first chamber to the second chamber through the intermediate region by applying an electric field or potential to or between the apertures of the first and second chamber.

The method may comprise passing ions from the first chamber to the second chamber or vice versa. The method may comprise passing ions from the first and/or second chamber to another region. This will depend on the geometry of the instrument.

The first chamber may e.g. comprise a transfer cell, a storage cell, a collision cell, a reaction cell, an ion activation cell, an ion mobility separation device or an ion gate.

The second chamber may (independently of the first chamber) e.g. comprise a transfer cell, a storage cell, a collision cell, a reaction cell, an ion activation cell, an ion mobility separation device or an ion gate.

In embodiments, the first and/or second chamber may comprise an ion mobility separation device. For instance, the first and/or second chamber may comprise a drift-time based ion mobility separation device or a travelling wave based ion mobility separation device. In embodiments, the first chamber may comprise a drift-time based ion mobility separation device and the second chamber may comprise a travelling wave based ion mobility separation device. It will be appreciated that the techniques described herein may find particularly utility in this context as the gas composition within an ion mobility separation device may need to be carefully controlled in order to obtain accurate ion mobility measurements, as the ion mobility separation depends on the interactions between the analyte ions and the ion mobility buffer gas. It will be appreciated that where the first and/or second chamber comprises an ion mobility separation device, the first and/or second gas may e.g. comprise nitrogen, or various other suitable buffer gases.

In embodiments, the first chamber may comprise an ion gate, such as a helium cell, and the second chamber may comprise an ion mobility separation device.

The intermediate region may comprise a plurality of electrodes and/or an ion guide for transferring ions through said intermediate region. Optionally, the method may comprise transferring ions between the first and second chambers through the plurality of electrodes and/or the ion guide.

There may be no regions or devices other than the intermediate region disposed between the first chamber and the second chamber. That is, the intermediate region may be, and typically is, the only region disposed between the first chamber and the second chamber, such that the first chamber and the second chamber are each adjacent to and separated from each other by the intermediate region. The first and second chambers are thus relatively close coupled via the intermediate region.

The intermediate region may generally contain a plurality of electrodes or other ion transfer optics. One or more electric fields or potentials may be applied to the plurality of electrodes in order to confine and/or transport ions. In particular, the intermediate region may comprise an RF ion guide. The method may comprise applying one or more RF potentials to a plurality of electrodes within the intermediate region in order to confine ions (radially) within the intermediate region. This may prevent ion losses in the intermediate region and ensure ions can be efficiently transferred between the first and second chambers. It will be appreciated that ions need not be transferred directly between the first and second chambers and the ion guide may also be used to transfer ions from the first and/or second chamber to a further chamber or region.

The method may comprise dynamically varying the pressure in the intermediate region during the course of an acquisition.

The method may comprise maintaining a minimum pressure difference between the intermediate region and the first and/or second chamber. The minimum pressure difference may be selected to be large enough to ensure that the gas outflow is (substantially only) from the first and second chambers into the intermediate region.

The method may additionally or alternatively comprise maintaining a maximum pressure difference between the intermediate region and the first and/or second chamber. The maximum pressure difference may be selected such that the pressure in the intermediate region is not so low that too large a pressure gradient is established, which may prevent efficient ion transport.

The pressure difference between the first and/or second chamber and the intermediate region may be in a range selected from the group consisting of: (i) <about 0.0001 mbar; (ii) about 0.0001-0.001 mbar; (iii) about 0.001-0.01 mbar; (iv) about 0.01-0.1 mbar; (v) about 0.1-1 mbar; (vi) about 1-10 mbar; (vii) about 10-100 mbar; (viii) about 100-1000 mbar; and (ix) >about 1000 mbar.

The pressure difference between the intermediate region and the first and/or second chamber may be maintained within a certain range. The minimum and/or maximum pressure differences may be such that transitional or viscous gas flow conditions exist between the first and second chambers and the intermediate region. Generally, the pressure difference range may depend on the instrument geometry e.g. the size of the chambers and the respective apertures and the length of the intermediate region and on the operating pressures within the regions.

The method may comprise dynamically varying the pressure in the intermediate region during the course of an acquisition so as to maintain the minimum and/or the maximum pressure difference.

The first chamber may be maintained at a pressure within a range selected from the group consisting of: (i) about 0.01-0.1 mbar; (ii) about 0.1-1 mbar; (iii) about 1-10 mbar; (iv) about 10-100 mbar; and (v) about 100-1000 mbar.

Similarly, the second chamber may (e.g. independently) be maintained at a pressure within a range selected from the group consisting of: (i) about 0.01-0.1 mbar; (ii) about 0.1-1 mbar; (iii) about 1-10 mbar; (iv) about 10-100 mbar; and (v) about 100-1000 mbar.

Generally, the first pressure in the first chamber may be substantially equal to, greater than, or less than the second pressure in the second chamber. The pressures in the first and second chambers will generally be substantially independent of each other.

The method may comprise operating the intermediate region at a pressure within the range $10^{-3}$ to $10^3$ mbar. For instance, the intermediate region may be operated at a pressure within a range selected from the group consisting of: (i) about 0.001-0.01 mbar; (ii) about 0.01-0.1 mbar; (iii) about 0.1-1 mbar; (iv) about 1-10 mbar; (v) about 10-100 mbar; and (vi) about 100-1000 mbar.

Generally, the pressure in the intermediate region will be similar to (but lower than) the pressures in the first and/or second chamber. For instance, the pressure in the intermediate region may be of the same order of magnitude as the pressure in the first and/or second chamber. In embodiments therefore, the intermediate region may also be operated at a pressure within the range of about $10^{-2}$ to $10^3$ mbar. The pressure in the intermediate region should be lower than that in the first and second chamber chambers but may generally be higher than that in other vacuum stages of the instrument, e.g. the pressure in the intermediate region may be higher than that in any quadrupole mass filtering or transfer optics and that of any mass analyser. It will be appreciated that there may be a local pressure minimum in the intermediate region between the first and second chambers.

The pressure in the intermediate region may be in the range of between about 0.1-0.9 or 0.5-0.9 times the pressure in the first and/or second chamber. The pressure in the intermediate region may be in a range selected from the group consisting of: (i) about 0.1-0.2 times the pressure in the first and/or second chamber; (ii) about 0.2-0.3 times the pressure in the first and/or second chamber; (iii) about 0.3-0.4 times the pressure in the first and/or second chamber; (iv) about 0.4-0.5 times the pressure in the first and/or second chamber; (v) about 0.5-0.6 times the pressure in the first and/or second chamber; (vi) about 0.6-0.7 times the pressure in the first and/or second chamber; (vii) about 0.7-0.8 times the pressure in the first and/or second chamber; and (viii) about 0.8-0.9 times the pressure in the first and/or second chamber.

The pressures in each of the first and second chambers and the intermediate region, and the pressure difference between the first and second chambers and the intermediate region may be such that transitional or viscous gas flow conditions exist. In general therefore, the pressure in the intermediate region may be high enough such that transitional or viscous gas flow conditions exist between the first and/or second chambers and the intermediate region.

The length of the intermediate region may be: (i) less than about 5 cm; (ii) less than about 1 cm; or (iii) less than about 0.5 cm. The length of the intermediate region may be between about 0.5-1 cm. It will be appreciated that these lengths are relatively short e.g. compared to conventional ion guides (which may be at least about 10 cm in length), such that the first and second chambers are relatively closely coupled with one another, and wherein the purpose of the intermediate region is essentially only to facilitate coupling of adjacent first and second chambers whilst keeping the first and second gases separate. It will be understood that the length of the intermediate region as used herein refers to the length between the first chamber and the second chamber, e.g. along which ions travel to pass from the first chamber to the second chamber (or vice versa)—for example, the length between the apertures of the first chamber and the second chamber through which ions and/or gas exit/enter the first and/or second chambers.

It will be appreciated that the methods for coupling gas-filled regions within a mass spectrometer or an ion mobility spectrometer according to any of the aspects or embodiments described herein may constitute or may extend generally to methods of mass or ion mobility spectrometry.

Hence, according to another aspect there is provided a method of mass or ion mobility spectrometry comprising a method of coupling gas-filled regions substantially as described herein in any aspect or embodiment.

The method of mass spectrometry may e.g. further comprise generating ions at an ion source, providing the generated ions to the first chamber and/or the second chamber, and passing the ions through the first chamber and/or the second chamber and through the intermediate region prior to a step of mass or ion mobility analysis. For instance, the method may comprise: (i) passing ions from the first chamber to the second chamber via the intermediate region; (ii) passing ions from the second chamber to the first chamber via the intermediate region; or (iii) passing ions from the first and/or second chamber to another region via the intermediate region.

The method may comprise applying an electric field to the intermediate region and/or between the first and second chambers in order to drive ions between the first chamber and the second chamber via the intermediate region.

Ions may be driven through or out of the intermediate region by one or more electric fields or potentials applied to electrodes of the intermediate region. For instance, the ions may be driven using one or more linear DC gradients, one or more transient DC potentials ("travelling waves") and/or one or more AC or RF potentials.

Ions may additionally or alternatively be driven from the first chamber to the second chamber through the intermediate region by applying an electric field or potential to or between the apertures of the first and second chamber.

The method may comprise passing ions from the first chamber to the second chamber or from the second chamber to the first chamber. The method may also comprise passing ions from the first and/or second chamber to another region, depending on the geometry of the mass spectrometer or ion mobility spectrometer.

According to another aspect there is provided a device for use in a mass or ion mobility spectrometer comprising:
a first chamber containing (in use) a first gas;
a second chamber containing (in use) a second gas; and
an intermediate region disposed between the first and second chambers, wherein the intermediate region is operated, in use, at a pressure below that of the first and second regions in order to prevent ingress of the first gas into the second chamber and/or of the second gas into the first chamber.

The device may further comprise one or more pumps configured to: maintain the first chamber, in use, at a pressure within the range of about $10^{-2}$ to $10^3$ mbar; and/or maintain the second chamber, in use, at a pressure within the range of about $10^{-2}$ to $10^3$ mbar; and/or maintain the intermediate region, in use, at a pressure within the range of about $10^{-3}$ to $10^3$ mbar and below the pressures at which each of the first and second chambers are operated.

The first and second chambers may each have a dedicated, independent gas supply for supplying the first and second gases respectively.

A (e.g. single) pump connected to the intermediate region may be used to maintain the pressures in each of the first and second chambers and the intermediate region (e.g. in combination with first and second gas supplies associated respectively with the first and second chambers). Additionally or alternatively, the first and/or second chamber may also be connected to a pump.

The first chamber may comprise a helium gate and the second chamber may comprise an ion mobility separation device. The first chamber may comprise a first ion mobility separation device and the second chamber may comprise a second ion mobility separation device.

The intermediate region may comprise a plurality of electrodes and/or an RF ion guide for transferring ions through said intermediate region.

The device may further comprise any or all of the features described herein in any aspect or embodiment, and particularly may be configured or arranged to perform a method substantially as described herein in any aspect or embodiment.

According to another aspect there is provided a mass or ion mobility spectrometer comprising a device substantially as described herein in any aspect or embodiment.

The mass or ion mobility spectrometer may further comprise any or all of the features described herein in any aspect or embodiment, and particularly may be configured or arranged to perform a method of mass or ion mobility spectrometry substantially as described herein in any aspect or embodiment.

According to another aspect there is provided a method for coupling gas-filled regions within a mass or ion mobility spectrometer comprising:
providing an intermediate region disposed between a first chamber containing a first gas and a second chamber containing a second gas; and
operating the intermediate region at a pressure below that of the first and second chambers so as to substantially prevent or reduce ingress of the first gas into the second chamber and/or of the second gas into the first chamber, wherein the pressure difference between the intermediate region and the first and second chambers is such that transitional or viscous gas flow conditions exist.

According to another aspect there is provided a mass or ion mobility spectrometer comprising:
a first chamber containing a first gas;
a second chamber containing a second gas; and
an intermediate region disposed between the first and second chambers, wherein the intermediate region is operated, in use, at a pressure below that of the first and second regions to prevent ingress of the first gas into the second chamber and/or of the second gas into the first chamber, and wherein the pressure difference between the intermediate region and the first and second chambers is such that transitional or viscous gas flow conditions exist.

It will be appreciated that the methods and/or spectrometers according to any of these aspects may also contain any or all of the features described elsewhere herein in any aspect or embodiment, at least to the extent that they are not mutually exclusive.

According to an embodiment the mass spectrometer may further comprise:
(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage optionally has an amplitude selected from the group consisting of: (i) about <50 V peak to peak; (ii) about 50-100 V peak to peak; (iii) about 100-150 V peak to peak; (iv) about 150-200 V peak to peak; (v) about 200-250 V peak to peak; (vi) about 250-300 V peak to peak; (vii) about 300-350 V peak to peak; (viii) about 350-400 V peak to peak; (ix) about 400-450 V peak to peak; (x) about 450-500 V peak to peak; and (xi) >about 500 V peak to peak.

The AC or RF voltage may have a frequency selected from the group consisting of: (i) <about 100 kHz; (ii) about 100-200 kHz; (iii) about 200-300 kHz; (iv) about 300-400 kHz; (v) about 400-500 kHz; (vi) about 0.5-1.0 MHz; (vii) about 1.0-1.5 MHz; (viii) about 1.5-2.0 MHz; (ix) about 2.0-2.5 MHz; (x) about 2.5-3.0 MHz; (xi) about 3.0-3.5 MHz; (xii) about 3.5-4.0 MHz; (xiii) about 4.0-4.5 MHz; (xiv) about 4.5-5.0 MHz; (xv) about 5.0-5.5 MHz; (xvi) about 5.5-6.0 MHz; (xvii) about 6.0-6.5 MHz; (xviii) about 6.5-7.0 MHz; (xix) about 7.0-7.5 MHz; (xx) about 7.5-8.0 MHz; (xxi) about 8.0-8.5 MHz; (xxii) about 8.5-9.0 MHz; (xxiii) about 9.0-9.5 MHz; (xxiv) about 9.5-10.0 MHz; and (xxv) >about 10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

According to an embodiment analyte ions may be subjected to Electron Transfer Dissociation ("ETD") fragmentation in an Electron Transfer Dissociation fragmendevice. Analyte ions may be caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions may comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenylanthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

According to an embodiment the process of Electron Transfer Dissociation fragmentation comprises interacting analyte ions with reagent ions, wherein the reagent ions comprise dicyanobenzene, 4-nitrotoluene or azulene.

BRIEF DESCRIPTION OF THE DRAWINGS

Various embodiments will now be described, by way of example only, and with reference to the accompanying drawings in which.

DETAILED DESCRIPTION

In many conventional or current instrument geometries different gas-filled regions are typically directly connected by an aperture such that some degree of mixing or leaking of gases is inevitable. However, in some regions, it is desired to prevent substantial mixing or leaking of gases. For example, in one known system, an augmented helium cell is provided immediately upstream of and in direct fluid communication with a nitrogen-filled ion mobility separation ("IMS") cell. The helium cell may provide a low loss interface to the high pressure ion mobility separation ("IMS") cell in the form of a gate for controlling ion entry into the ion mobility separation ("IMS") device. Both of these cells operate at relatively high pressures, e.g. in the range between about $10^{-2}$ and $10^3$ mbar. Depending on the direction of the pressure gradient, there may be a risk of helium gas leaking into the IMS cell, thus modifying the composition of the IMS buffer gas, and hence the nature of the ion mobility separation. There may also be a risk of nitrogen gas outflowing into the helium cell, which at relatively high pressures, may make it difficult to drive ions into the IMS cell, against the outflow. Trying to force ions against this outflow may be undesirable as this may lead to unwanted ion activation due to collisions with the buffer gas in the IMS cell, and the initial velocity distribution may cause a loss of resolution in the IMS measurement. A better situation would be to have the two regions containing pure gas. Similar considerations apply to various other situations where it is important for the gas composition and/or gas pressure in adjacent regions to be carefully controlled by avoiding any intermixing of the gases.

Figure 1:
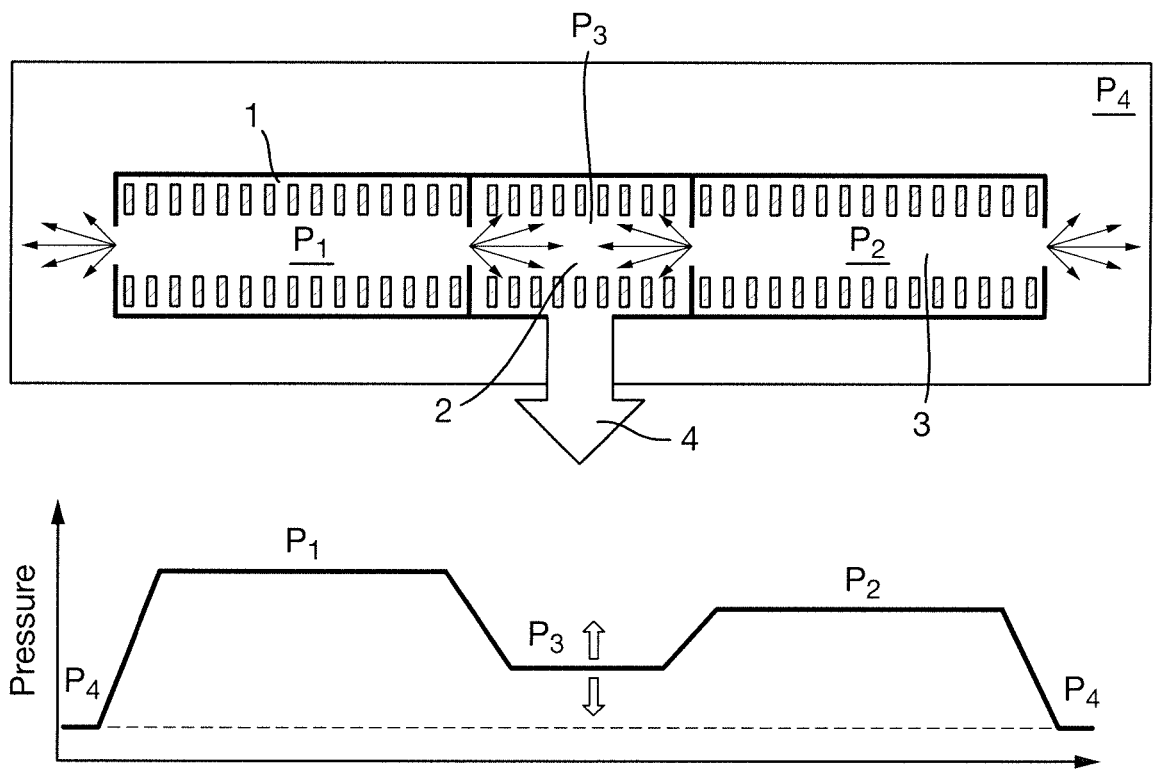
FIG. 1 shows a device for coupling two gas-filled chambers according to an embodiment.

FIG. 1 shows an embodiment including an intermediate pressure chamber that may be used for coupling two gas-filled regions in a mass (or ion mobility) spectrometer and for preventing intermixing of gases. As shown in FIG. 1, the first region comprises a first enclosed chamber 1 containing a first gas and is operated at a first pressure P1. The second region comprises a second enclosed chamber 3 containing a second gas and is operated at a second pressure P2. Generally, the pressures may be such that P1=P2, P1<P2 or P1>P2.

The first chamber 1 and the second chamber 3 each have a dedicated, independent gas supply (not shown) for supplying the first and second gases. The gas composition and pressure in the first 1 and second 3 chambers may be controlled through the gas supply, and/or through pumping applied to an intermediate region 2 disposed between the first and second regions, and optionally any additional pumping applied to the first chamber 1 and/or the second chamber 3. It will be appreciated that various gas supply manifolds and pumping arrangements may be used in conjunction with the techniques described herein.

Cross-contamination of the first and second gas may be prevented by providing the intermediate region 2 between the first chamber 1 and the second chamber 3 and operating the intermediate region 2 at a third pressure P3, wherein P3 is lower than both P1 and P2. The intermediate region 2 acts merely to couple the first chamber 1 to the second chamber 3 and prevent gas intermixing, and may therefore be referred to as a "bridge cell" or a "gas bridge". The intermediate region 2 is generally therefore relatively short, and may e.g. have a length (extending between the first chamber 1 and the second chamber 3) of less than about 5 cm, for example, between about 0.5-1 cm. It will be appreciated that the length of the gas bridge is relatively short compared e.g. to a conventional ion guide of typical length around 10 cm or more.

The variation in pressure along the length of the device is also schematically plotted at the bottom of FIG. 1, with the pressure P4 representing the background gas pressure e.g. in the high vacuum stages of the mass spectrometer.

By maintaining the intermediate region 2 at a lower pressure P3 relative to the first 1 and second 3 adjacent chambers gases from the first region and second region will (only) flow along the pressure gradient into the intermediate region 2. The intermediate region 2 may thus contain a mixture of the first and second gases but these will not flow against the pressure gradients (back) into the first chamber 1 or the second chamber 3. In this way, the purity of the gases within the first chamber 1 and second chamber 3 can be maintained.

As mentioned above, the pressure P3 in the intermediate region 2 may be regulated by appropriate pumping applied to the intermediate region 2. For example, a pump 4 having a variable pumping speed may be provided for use in controlling the pressure P3 in the intermediate region 2. The pressure P3 may be dynamically altered during the course of an acquisition, e.g. to keep the pressure difference between the intermediate region 2 within a certain desired range below the pressure in the first chamber 1 and/or the second chamber 2. The gas composition and/or the pressure in the first region 1 and/or the second region 3 may also be dynamically altered during the course of an acquisition, with the pressure in the intermediate region 2 altered accordingly.

It will be appreciated that there is a local minimum in pressure in the intermediate region 2. However, it will also be appreciated, e.g. from the plot shown in FIG. 1, that the pressure P3 in the third region 2 is still elevated relative to the background gas pressure P4. The pressure P3 in the intermediate region 2 may generally be of a similar order of magnitude to, i.e. just slightly lower than, the pressure in the first chamber 1 and/or the second chamber 3. The gas pressures P1, P2, P3 may each be sufficiently high such that transitional or viscous flow conditions exist between each of the first chamber 1 and the second chamber 3 and the intermediate region 2. Transitional or viscous flow conditions may be characterised as having a relatively low Knudsen number, for instance, of less than about 0.5 or less than about 0.1, respectively. For pressures in the range of about $10^{-2}$ mbar upwards and for typical first and second chambers having apertures of around 1 mm diameter, the Knudsen number of the flow of the first and second gases into the intermediate region 2 may be less than about 5. By keeping the pressure difference between the intermediate region 2 and the first chamber 1 and second chamber 3 relatively low it is possible to transport ions out of the intermediate region 2 using relatively low electric fields thereby minimising unintentional ion activation. For instance, the pressure difference may be kept within a range so that it is just high enough to set up the desired gas flow out of the first region 1 and the second region 3 into the intermediate region 2. In general, depending on the instrument geometry, ions may be transported to the intermediate region 2 from either the first chamber 1 and/or the second chamber 3 and may be transported from the intermediate region 2 to either the first chamber 1 and/or the second chamber 3.

It is also contemplated that the techniques and devices described herein may be used in geometries containing more than two gas-filled regions coupled to a single pumped intermediate region 2. In these cases, ions may be transported to and from the intermediate region 2 from any or all of the adjacent gas-filled regions.

The first chamber 1 and the second chamber 3 may generally comprise any gas-filled chamber. For example, each of the first chamber 1 and second chamber 3 may each comprise an ion transfer cell, an ion storage cell, a collision cell, a reaction or activation cell or an ion mobility cell. As shown in FIG. 1, the first chamber 1 and the second chamber 3 may generally each comprise a plurality of electrodes for guiding or otherwise manipulating ions. For instance, the first chamber 1 may comprise an RF ion guide.

The intermediate region 2 may also contain a plurality of electrodes or transfer optics such as an ion guide, as shown for the embodiment illustrated in FIG. 1. For example, the intermediate region 2 may comprise an RF ion guide in order to prevent ion losses within this region. Ions may thus be transported between the first chamber 1 and second chamber 3 using one or more electric fields applied to the electrodes within the intermediate region 2 and/or to the electrodes (or e.g. electrodes at the apertures to) the first chamber 1 and/or second chamber 3. These electric fields may generally comprise travelling waves or static fields as is known in the art.

Figure 2:
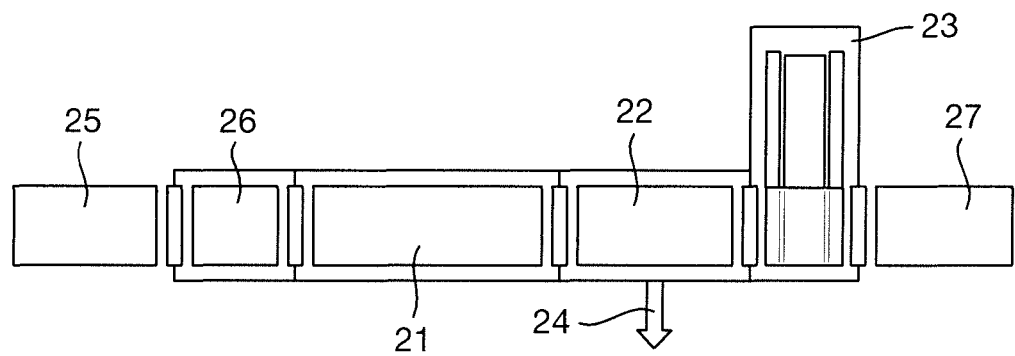
FIG. 2 shows one possible instrument geometry incorporating a device such as that which is shown in FIG. 1.
Figure 3:
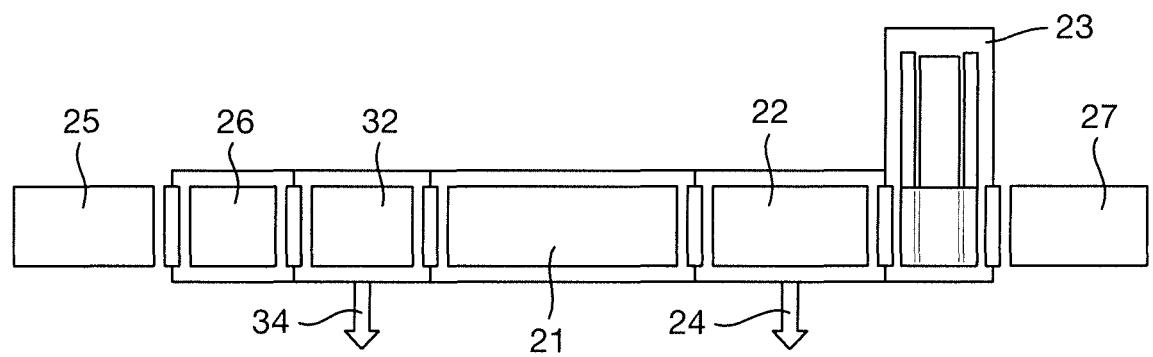
FIG. 3 shows another possible geometry incorporating a device such as that which is shown in FIG. 1.

As discussed above, one potential form of the device illustrated in FIG. 1 is to provide an enhanced helium gate for use in interfacing to an ion mobility separation device. In this case, the first chamber 1 comprises a helium gate (such that the first gas is helium) and the second chamber 3 comprises an ion mobility separation device (such that the second gas comprises nitrogen, or some other suitable buffer gas). However, it will be appreciated that a device of the general type described herein may also be incorporated into various other geometries. FIGS. 2 and 3 illustrate two possible instrument geometries where the techniques and devices described herein may find utility.

Referring to FIG. 2, a device similar to that which is shown in FIG. 1 may be used to couple a first ion mobility separation device 21 containing a first buffer gas to a second ion mobility separation device 23 containing a second buffer gas. A bridge cell 22 connected to a variable speed pump 24 (the bridge cell being of the general type described herein, e.g. in relation to FIG. 1) may thus be provided to allow coupling of the first ion mobility separation device 21 to the second ion mobility separation device 23 without intermixing of the buffer gases. As the composition of the ion mobility separation buffer gas determines the nature and strength of the ions' interactions within the ion mobility separation device (and hence the amount of separation, and the measured drift times), it will be appreciated that it may be particularly important in this context to prevent contamination of the buffer gas.

The first ion mobility separation device 21 may e.g. comprise a linear field device and the second ion mobility separation device 23 may e.g. comprise a travelling wave device, which may generally be either a linear or a cyclic travelling wave separation device. The instrument may optionally, as depicted in FIG. 2, further include various other components, such as an ion trap 25, a helium cell 26 upstream of the first ion mobility separation device 21 and a transfer device 27 downstream of the second ion mobility separation device 23 for transporting ions to a detector or mass analyser. It will be understood, however, that these components are merely exemplary and are not intended to be limiting.

FIG. 3 illustrates another example, where a gas bridge is also used to couple a helium cell to a linear field ion mobility separation device. The instrument geometry shown in FIG. 3 therefore corresponds to that shown in FIG. 2 except that a second bridge cell 32 connected to a second pump 34 is provided between the helium cell 26 and the first ion mobility separation device 21. It will be appreciated that multiple successive devices of the general type described herein and e.g. shown in FIG. 1 (i.e. intermediate pressure regions or gas bridges) may be used to couple multiple gas-filled regions in series, and that FIGS. 2 and 3 merely illustrate two possible configurations.

The intermediate region or bridge cell 2 illustrated in FIG. 1 comprises a third chamber connected to a vacuum pump. However, various other arrangements are also contemplated.

Figure 4:
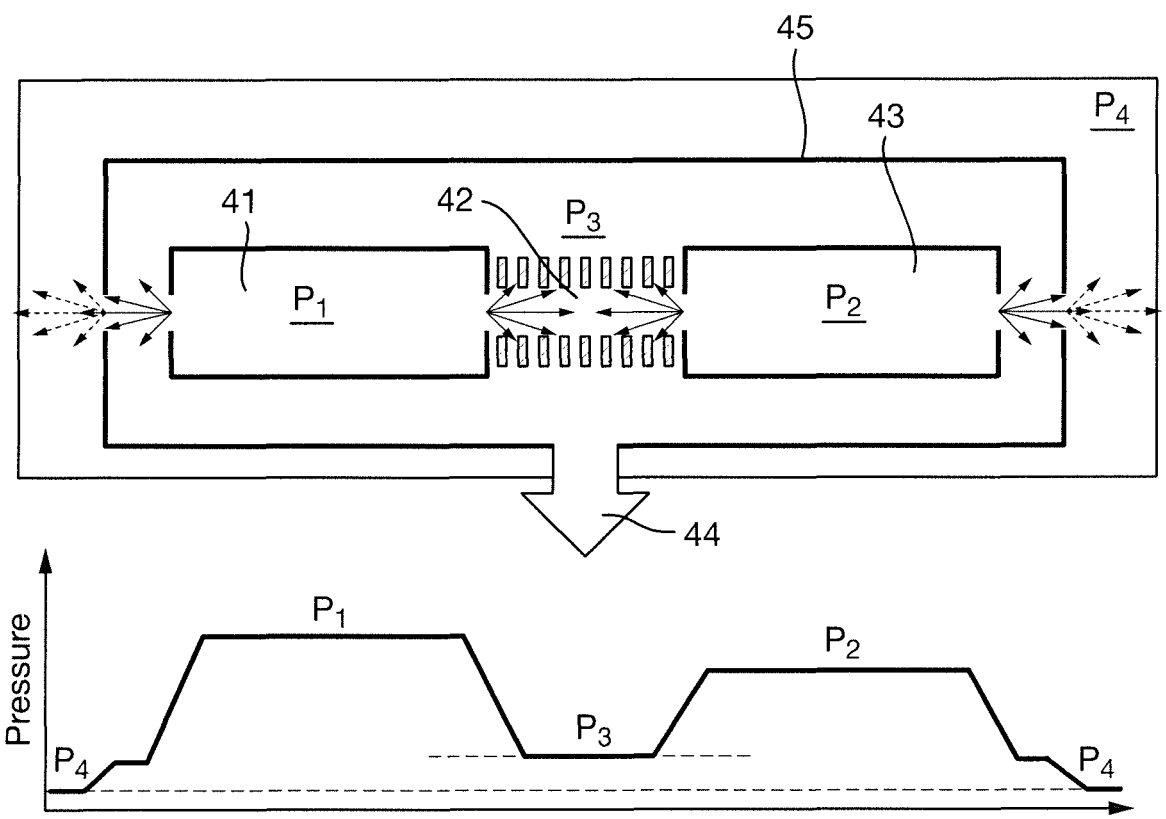
FIG. 4 shows a device for coupling two gas-filled chambers according to a further embodiment.

For instance, FIG. 4 shows another device for coupling a first chamber 41 and a second chamber 43. In the device of FIG. 4, the first 41 and second 43 chambers are each enclosed within a larger chamber 45. An ion guide 42 is disposed in the larger chamber 45 intermediate between the first chamber 41 and the second chamber 43. Pumping 44 is provided to the larger chamber 45 such that the intermediate region of the chamber 45 containing the ion guide 42 is maintained at a reduced pressure P3 relative to the pressure P1 in the first chamber 41 and the pressure P2 in the second chamber 43. Thus, the portion of the larger chamber 45 defined between the first chamber 41 and the second chamber 43 (and containing the ion guide 42) provides a gas bridge that acts in a similar manner to the device shown in FIG. 1 (and may therefore be used in similar contexts). The bottom of FIG. 4 shows a plot of the pressure variation along the length of the instrument.

Figure 5:
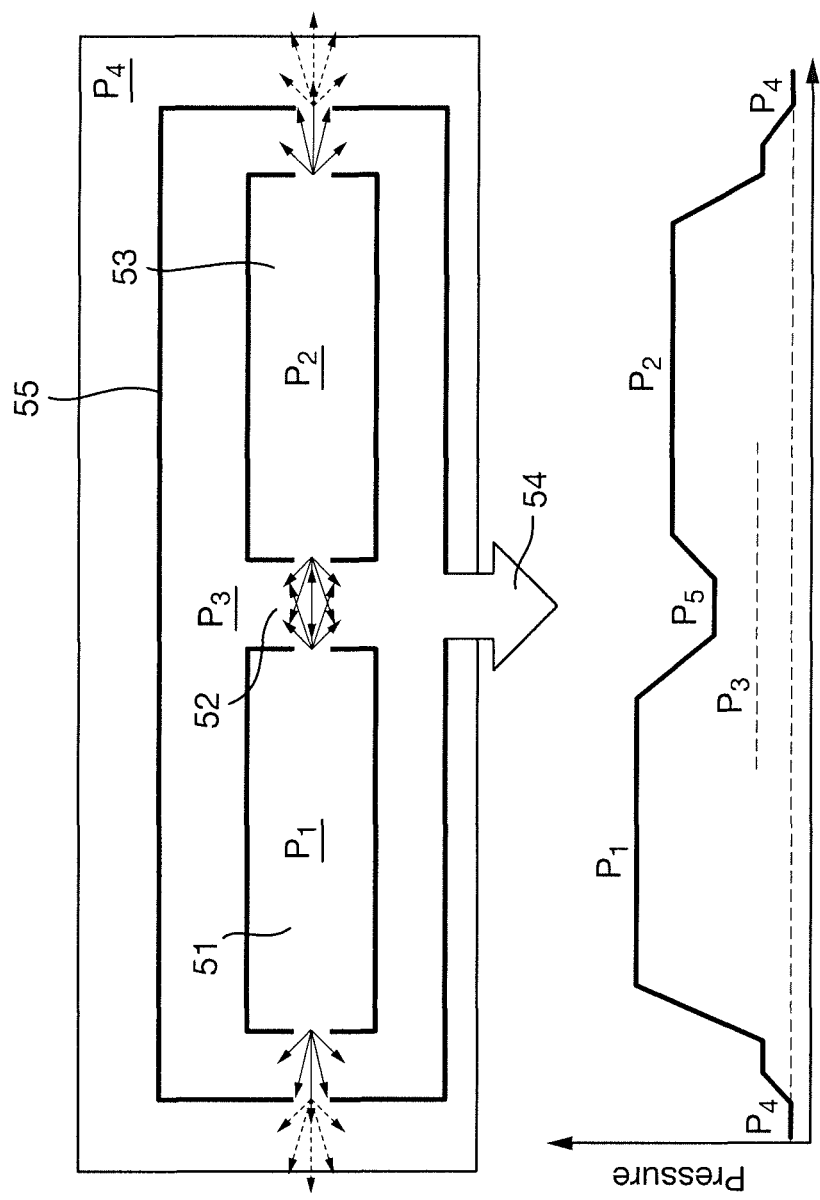
FIG. 5 shows a device for coupling two gas-filled chambers according to a yet further embodiment.

FIG. 5 shows another device for coupling first and second regions, similar to that which is shown in FIG. 4 but wherein no intermediate ion guide is provided. As with the device of FIG. 4, in the FIG. 5 device a first gas filled chamber 51 and a second gas-filled chamber 53 are provided within a larger chamber 55, with the larger chamber 55 being pumped to provide an intermediate region or gas bridge 52 of reduced pressure between the first chamber 51 and the second chamber 53. However, in the FIG. 5 device, there is no ion guide between the first chamber 51 and the second chamber 53. In order to mitigate potential ion losses the opposing apertures of the two gas-filled chambers 51,53 may be arranged so as to be relatively close together (e.g. closer than 1 cm, or even closer than 0.5 cm) so that ions can be driven from one region to another substantially without loss merely by applying voltage differences between the two aperture plates.

It will be appreciated that having the opposing apertures of the two gas-filled chambers 51,53 in such close proximity may create a pumping constriction that acts to create a locally higher pressure P5 in the intermediate region 52 between the chambers 51,53 (i.e. higher relative to the pressure P3 elsewhere within the larger chamber 55, but still lower than the pressures P1 and P2 in the first and second chambers, as shown schematically in the plot of pressure along the length of the device shown at the bottom of FIG. 5). Hence, the gas from the first chamber 51 and the second chamber 53 will flow into this region 52, and the mixed gas will then be pumped from the larger chamber 55 by pump 54.

Although in the embodiments described above the gases in the two regions are generally different, it will also be appreciated that devices of the type generally described above in relation to FIGS. 1, 4 and 5 may similarly be used to prevent unwanted ingress of gases even where the gases in the first and second regions are the same. For instance, this may help avoid pressure fluctuations within the first and second regions. This may be useful where the first and/or second chambers contain ion activation regions.

Although the present invention has been described with reference to certain embodiments, it will be understood by those skilled in the art that various changes in form and detail may be made without departing from the scope of the invention as set forth in the accompanying claims.

The invention claimed is:

1. A method for coupling gas-filled regions within a mass spectrometer or an ion mobility spectrometer comprising:
   providing an intermediate region disposed between a first chamber containing a first gas and a second chamber containing a second gas;
   operating said intermediate region at a pressure below that of said first and second chambers so as to substantially prevent or reduce ingress of said first gas into said second chamber or of said second gas into said first chamber; and
   dynamically varying said pressure in said intermediate region during the course of an acquisition so as to maintain a minimum or maximum pressure difference between said intermediate region and said first chamber or said second chamber.

2. A method as claimed in claim 1, comprising:
   operating said first chamber at a pressure within the range of about $10^{-2}$ to $10^3$ mbar; or
   operating said second chamber at a pressure within the range of about $10^{-2}$ to $10^3$ mbar; or
   operating said intermediate region at a pressure within the range of about $10^{-3}$ to $10^3$ mbar and below the pressures at which each of said first and second chambers are operated.

3. A method as claimed in claim 1, wherein said first chamber has a dedicated gas supply for supplying said first gas or wherein said second chamber has a dedicated gas supply for supplying said second gas.

4. A method as claimed in claim 1, wherein said first and second chambers are enclosed within a further chamber containing said intermediate region.

5. A method as claimed in claim 1, wherein said intermediate region comprises a third chamber.

6. A method as claimed in claim 1, wherein said first chamber or said second chamber comprises an ion mobility separation device.

7. A method as claimed in claim 1, wherein said first chamber comprises an ion gate.

8. A method as claimed in claim 1, wherein said intermediate region comprises a plurality of electrodes or an ion guide for transferring ions through said intermediate region.

9. A method as claimed in claim 1, wherein the length of said intermediate region is: (i) less than about 5 cm; (ii) less than about 1 cm; or (iii) less than about 0.5 cm.

10. A method for coupling gas-filled regions within a mass spectrometer or an ion mobility spectrometer comprising a first chamber containing a first gas, a second chamber containing a second gas, wherein said first and second chambers are enclosed within a further vacuum chamber of the mass spectrometer, said further vacuum chamber containing an intermediate region disposed between said first chamber and said second chamber, wherein the method comprises:
   operating said first chamber at a pressure within the range of about $10^{-2}$ to $10^3$ mbar;
   operating said second chamber at a pressure within the range of about $10^{-2}$ to $10^3$ mbar;
   operating said intermediate region at a pressure within the range of about $10^{-3}$ to $10^3$ mbar and below the pressures at which each of said first and second chambers are operated so as to substantially prevent or reduce ingress of said first gas into said second chamber or of said second gas into said first chamber;
   maintaining a minimum or maximum pressure difference between said intermediate region and said first chamber or said second chamber; and
   dynamically varying said pressure in said intermediate region during the course of an acquisition so as to maintain said minimum or said maximum pressure difference.

* * * * *